United States Patent [19]

Jung

[11] Patent Number: 5,012,227

[45] Date of Patent: Apr. 30, 1991

[54] WARNING DEVICE FOR LIQUID LEVEL IN DRIPPING BOTTLE

[76] Inventor: Chou K. Jung, No. 16-2, Alley 12, Lane 106, Pao Chien Road, Chung Ho City Taipei Hsien, Taiwan

[21] Appl. No.: 425,671

[22] Filed: Oct. 23, 1989

[51] Int. Cl.⁵ .............................................. G08B 21/00
[52] U.S. Cl. .................................... 340/618; 340/619; 128/DIG. 13; 73/293
[58] Field of Search .............................. 340/618, 619; 128/DIG. 13; 73/293; 250/577

[56] References Cited

U.S. PATENT DOCUMENTS

| | | | |
|---|---|---|---|
| 3,588,859 | 4/1969 | Petree | 340/620 |
| 3,939,360 | 2/1976 | Jackson | 340/620 X |
| 4,014,010 | 3/1977 | Jinotti | 340/619 |
| 4,378,014 | 3/1983 | Elkow | 128/DIG. 13 X |
| 4,749,988 | 6/1988 | Berman et al. | 340/620 X |
| 4,788,444 | 11/1988 | Williams | 340/619 X |

Primary Examiner—Joseph A. Orsino
Assistant Examiner—Jeffery A. Hofsass
Attorney, Agent, or Firm—Esso Int'l Patent and Trademark Office

[57] ABSTRACT

It is a warning device for a given liquid level in any dripping bottle; the device is furnished with a photo-electronic sensor, which can, through a detecting hole, sense the liquid level of a dripping bottle, and then sends a signal to a control circuit to drive a buzzer to generate a sound signal, whereby the nurse or the like is to be reminded that the liquid will be used up soon.

2 Claims, 2 Drawing Sheets

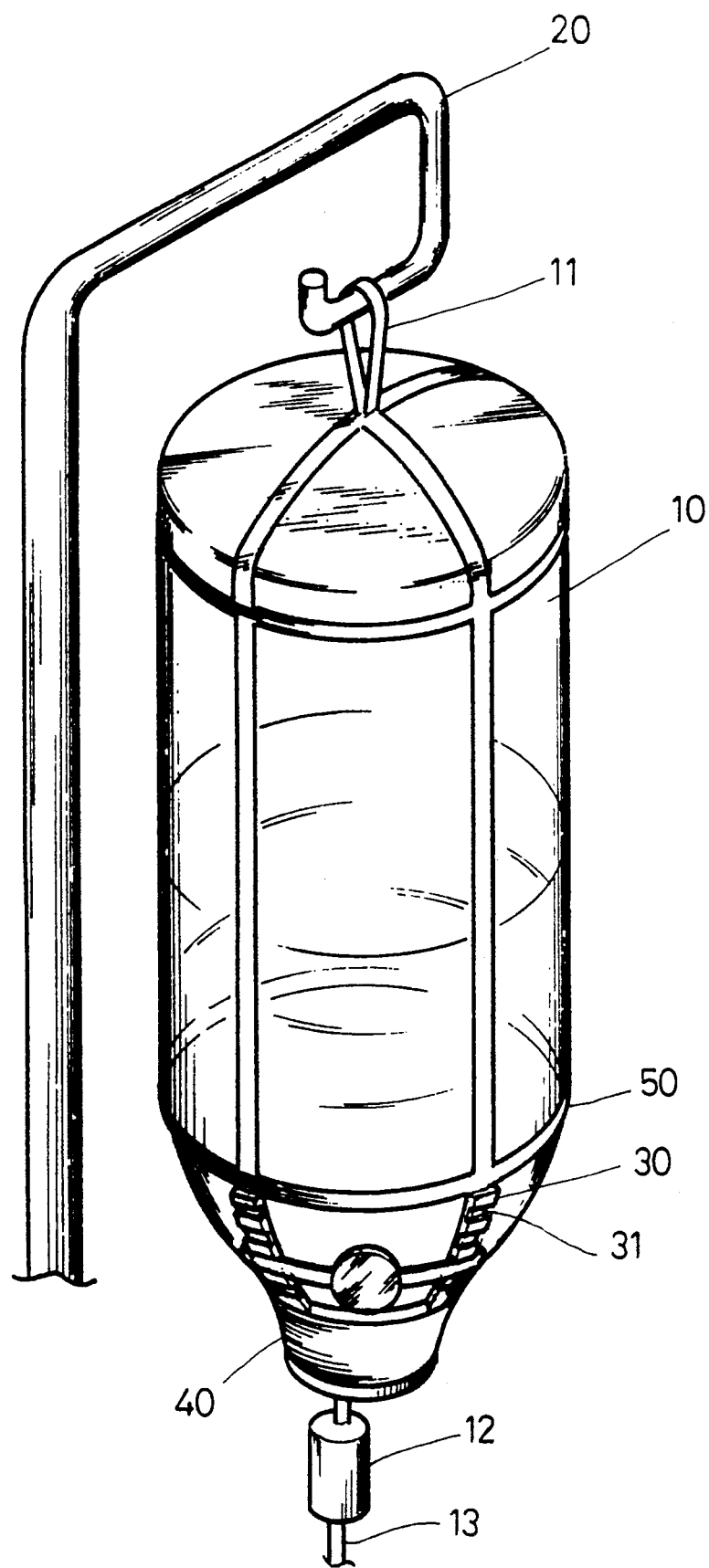
FIG·1

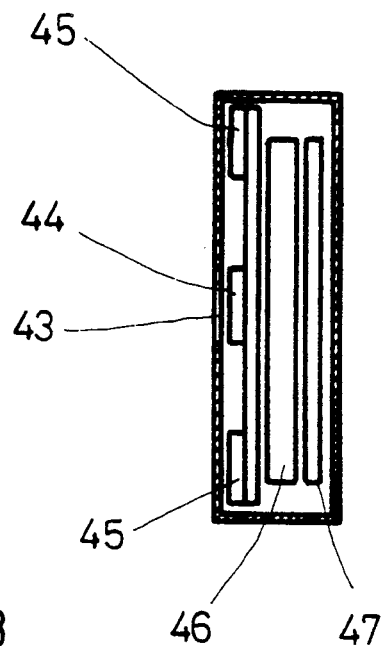
FIG·3
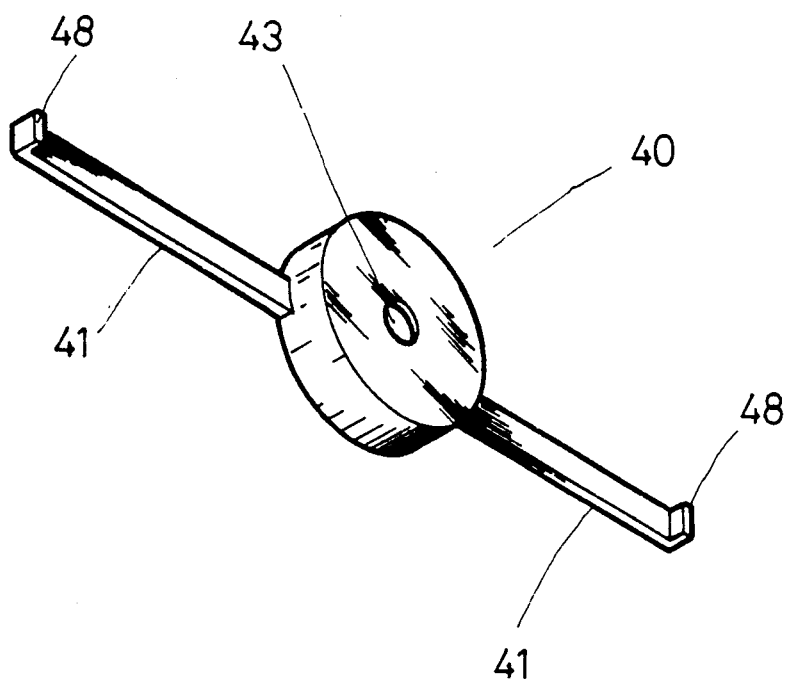
FIG·2

WARNING DEVICE FOR LIQUID LEVEL IN DRIPPING BOTTLE

BACKGROUND OF THE INVENTION

Regarding the warning devices for the dripping bottle in intravenous injection in the prior art, there are Spani's "Empty Container Detectar" U.S. Pat. No. 4,665,391; jinotti's "Fluid-dispensing Apparatus Having Level Control and Alarm Means" U.S. Pat. No. 4,014,010; Deltour's "Drop Monitor", etc. Among the aforesaid inventious, Spani's and Jinotti's inventious are used to detect the fluid level scales by means of photoelectric transducers being installed across a fluid container; one of the photoelectric transducers is associated with the fluid container above the fluid level in the container to establish a reference signal corresponding to the condition wherein the light path is not refracted or attenuated by the presence of a fluid. Electrical means are provided to connect the first photoelectric transducer to the second photoelectric transducer to linearize and normalize the reference signal with a control signal generated by another photoelectric transducer. A comparator is associated with the photoelectric transducer, and connected to an alarm, which indicates when the control signal is substantially equivalent to the reference signal, and thus indicating the lowering of the fluid level below the light path of the first photoelectric transducer.

In Deltour's (U.S. Pat. No. 3,563,090), the structure and design of the "Drop Monitor" is similar to Spani's invention. The light source and the photo-resistive cell are installed at one side of the drop observation tube 24 instead of being installed on the same level. On the opposite side of the light source and the photo-resistive cell, there installed a mirror so as to let a light pass through a medium surface, and then the light is reflected back to the photo-resistive cell.

SUMMARY OF THE INVENTION

This invention relates to a warning device for liquid level in a dripping bottle, and particularly it relates to a safety and convenient prewarning device, which mainly comprises a detecting unit with a soft belt extended from opposite edges of the detecting unit; both ends of the soft belt are furnished with fastening hooks respectively so as to facilitate the detecting unit to be attached on the grooves of a parallel frame. The detecting unit is attached to one side of a dripping bottle. The detecting unit includes a photo-electronic sensor, a control circuit and a buzzer. Whenever the liquid level of a dripping bottle is moved to a level and sensed by the photo-electronic sensor, the buzzer will send out a sound signal to remind a nurse or the like to see the dripping bottle. Furthermore, another feature of the present is that the position of the detecting unit on the bottle may be changed, if necessary.

BRIEF DESCRIPTION OF THE DRAWINGS

FIG. 1 is a perspective view of an embodiment according to the present invention.

FIG. 2 is a perspective view of the detecting unit in the present invention.

FIG. 3 is a sectional view of the detecting unit shown in FIG. 2.

DETAILED DESCRIPTION

FIG. 1 illustrates a perspective view of the present invention, in which the dripping bottle 10 is used for containing salt water or other nutritious liquid. The top of the dripping bottle 10 has a hook 11 for hanging the dripping bottle 10 on a supporting frame 20. The bottom of the dripping bottle is connected with a buffer tube 12, which is further connected with a tube 13 with an injection needle connected on the other and thereof. One of the lower side of the dripping bottle 10 is mounted with an encircling frame 30; the outer surface of the encircling frame 20 is furnished with a plurality of grooves 31, in which the fastening hooks 48 of the detecting unit 40 are to fasten. As shown in FIG. 2, a soft flexible belt structure 41 includes two flat belt sections extending from the sensing portion of the detecting unit 40. Both ends of the soft belt structure 41 are furnished with fastening hooks 48 respectively so as to facilitate the same to be fastened in the grooves 31. Hooks 48 are adapted to engage edge areas of strips 30 so that the flat belt sections are in taut conditions for supporting the sensor portion of detecting unit 40 flat against the bottle surface. The detecting unit 40 includes a photoelectronic sensor 44, a control circuit 45, a battery 46, and a buzzer 47. The center of the detecting unit has a detecting hole 43 with a photo-electronic sensor 44 therein for sensing the liquid level inside the dripping bottle 10 as shown in FIG. 3. The FIG. 3 assembly can be considered as the sensor body portion of the liquid level detecting unit.

When the dripping bottle is used for injection, the dripping bottle should first be mounted in reverse position inside a crating belt 50 so as to let the liquid in the bottle slowly drip through a tube 13 and an injection needle to a person's body. As soon as the level of liquid in the dripping bottle reaches the opposite position of the detecting hole 43, the photo-electronic sensor 44 will generate a signal to transmit into the control circuit 45, which will send a signal to cause the buzzer 47 to generate a sound signal to remind a nurse or the like that the liquid in the bottle will soon be used up. The photoelectronic sensor 44 and the control circuit 45 are made of CMOS. Since the battery 46 is very small in size, it can be sandwiched inside the detecting unit 40. The whole detecting unit 40 is a very small unit with high sensitivity, and it can be mounted at different position so as to sense the liquid level in different condition, and therefore it is deemed a practical and novel device.

I claim:

1. In combination, a liquid-containment bottle (10) adapted to be hung in a vertical position for intravenous injection of a contained liquid into a patient, said bottle including a lower liquid discharge neck portion that converges toward the bottle axis in the downward direction;

a frame structure encircling the neck portion of the bottle, said frame structure including two downwardly-extending strips (30) lying against the bottle surface in spaced-apart relation, each said strip having a plural number of transverse grooves (31) spaced therealong;

a liquid level detecting alarm unit that includes a sensor body adapted for removable attachment, and also positioned flat against the outer surface of the bottle, and a flexible belt structure connected to said sensor body;

said belt structure comprising two oppositely-extending flat belt sections, each belt section having a first end thereof connected to the sensor body and a second free end thereof spaced from the sensor body;

each belt section having a width dimension such that the width dimension of the belt section is the same as the width dimension of each said groove (31); whereby the sensor body can be positioned against the bottle surface with one of the flat belt sections snapped into a groove in one of the strips, and with the other flat belt section snapped into a groove in the other strip;

said belt sections being detachably connected to the strips so that belt sections are in a taut condition supporting the sensor body against the bottle surface.

2. In combination, a liquid-containment bottle (10) adapted to be hung in a vertical position for intravenous injection of the contained liquid into a patient, said bottle including a lower portion that forms a liquid discharge opening for a downflow of liquid from the bottle;

a frame structure encircling the neck portion of the bottle, said frame structure including two downwardly-extending strips (30) lying against the bottle surface in spaced-apart relation, each said strip having a plural number of transverse grooves (31) spaced therealong;

a liquid level detecting alarm unit that includes a sensor body adapted for removable attachment, and also positioned flat against the outer surface of the bottle, and a flexible belt structure connected to said sensor body;

said belt structure comprising two oppositely-extending flat belt sections, each belt section having a first end thereof connected to the sensor body and a second free end thereof spaced from the sensor body, the free end of each belt section being turned generally normal to the flat plane of the belt section to form a hook;

each belt section having a width dimension which is the same as the width dimension of each said groove (31); whereby the sensor body can be positioned against the bottle surface with one of the flat belt sections snapped into a groove in one of the strips, and with the other flat belt section snapped into a groove in the other strip;

the belt structure being such that the hooks on the belt sections are engagable against edge areas of the strips to maintain the belt sections in a taut condition supporting the sensor body against the bottle surface.

* * * * *